(12) United States Patent
Brotzeller et al.

(10) Patent No.: US 6,896,247 B2
(45) Date of Patent: May 24, 2005

(54) X-RAY ANALYSIS SYSTEM WITH HUMIDIFIED SAMPLE

(75) Inventors: Uwe Georg Brotzeller, Ettlingen (DE); Hans Leitz, Karlsruhe (DE)

(73) Assignee: Bruker Axs GmbH, Karlsruhe (DE)

( * ) Notice: Subject to any disclaimer, the term of this patent is extended or adjusted under 35 U.S.C. 154(b) by 308 days.

(21) Appl. No.: 10/197,427

(22) Filed: Jul. 18, 2002

(65) Prior Publication Data
US 2004/0013228 A1 Jan. 22, 2004

(51) Int. Cl.⁷ .......................... B01F 3/04; G01N 23/20
(52) U.S. Cl. .................. 261/128; 261/63; 261/104; 261/129; 261/133; 261/154; 378/80
(58) Field of Search .................. 261/44.1, 63, 99, 261/104, 107, 128–131, 133, 136, 137, 152, 154; 378/45, 47, 70, 79, 80, 208

(56) References Cited

U.S. PATENT DOCUMENTS

| | | | | |
|---|---|---|---|---|
| 3,532,270 A | * | 10/1970 | Schoen Jr. ................ | 236/44 R |
| 3,735,559 A | * | 5/1973 | Salemme ...................... | 95/52 |
| 4,263,510 A | * | 4/1981 | Ciccarelli et al. ............. | 378/46 |
| 4,821,303 A | * | 4/1989 | Fawcett et al. ............... | 378/80 |
| 5,390,230 A | * | 2/1995 | Chang ......................... | 378/80 |
| 6,748,048 B2 | * | 6/2004 | Dosho ......................... | 378/79 |

* cited by examiner

Primary Examiner—Scott Bushey
(74) Attorney, Agent, or Firm—Paul Vincent

(57) ABSTRACT

An X-ray analysis system controls the humidity of a sample. The analysis system has a device for dividing a gas flow stream into two portions and for submerging a membrane humidifier tube, containing one of the gas flows, in a water bath in which the gas passing through that tube is moisturized to a desired degree. The two gas flows are subsequently reunited at a controlled temperature to provide for combined moisturized gas at a desired temperature and humidity. The gas is then sprayed onto the sample and an excess moisturized gas vented from the chamber to maintain a moisturize gas sample without condensation of water on or near the sample. This system and a method for its use allow measurements of samples to be made as a function of humidity and temperature over wide ranges of these parameters under highly stable conditions in a straightforward manner which are not susceptible to malfunction and which can be produced and operated at low cost.

19 Claims, 2 Drawing Sheets

X-RAY ANALYSIS SYSTEM WITH HUMIDIFIED SAMPLE

BACKGROUND OF THE INVENTION

The invention concerns an X-ray analysis system for controlling the humidity of a sample, a humidifying system to humidify gases for use in such X-ray systems, as well as a method for operating an X-ray analysis system to control the humidity of a sample.

In performing X-ray diffraction measurements under certain conditions and with certain samples it is often desirable to perform measurements at non-ambient relative humidity (rh). Samples of interest for study under changing relative humidity conditions include pharmaceuticals, minerals (clays), zeolites as well as various fine chemicals. Pharmaceuticals and chemical materials often undergo phase transitions that are either humidity or temperature driven and dependent. For example, certain zeolites activate or deactivate their docking sites in the presence of moisture to change their catalyst capability. This phenomenon is temperature dependent. Similarly, clay minerals swell and interact with water vapor in a temperature related fashion. Thus, materials of interest to such industries need to be investigated at elevated humidity and elevated temperature. In particular, certain physical properties of such materials change as a function of humidity. These physical properties include lattice spacing, crystal volume, weight, density, electrical conductivity or resistance, electrical capacitance, biological activity as well as their optical transparency. In addition to the substances mentioned above, such changes are particularly important for investigations of cosmetics, textiles, polymers, fertilizer, explosives, food, desiccants, and paper.

Apparatus capable of generating a humidified atmosphere typically rely on the use of gases to which a certain control degree of water (water vapor) has been added. The properties and performance of such devices are defined in terms of certain characteristic parameters. These include the saturation vapor pressure Ps corresponding to the maximum possible partial pressure of water vapor at a given air temperature. This parameter is temperature dependent and dictates the largest degree of water vapor that can be contained in a certain amount of air at a given temperature. Other parameters of critical interest to such measurements include the absolute humidity corresponding to the water vapor content. This parameter can be given as a mixing ratio in units of grams per kilogram and is related to the concentration of water vapor (e.g. in grams per cubic meter or as a percentage of a certain volume) wherein these volume and mass related quantities are temperature and pressure dependent. The dew point temperature Dp in degrees centigrade gives an additional absolute measurement of humidity. There is a direct relationship between the dew point temperature and the saturation vapor pressure. The dew point temperature is that temperature at which the saturation vapor pressure (or saturation concentration) of the water is reached. Therefore, an indication of the dew point temperature at atmosphere pressure is a unique indication of humidity. In many applications, the convenient figure of merit for designating humidity is the relative humidity $h_{rel}$, in percent. This quantity is the ratio between the absolute moisture and the absolute moisture for saturation at a given temperature and pressure. Since the saturation vapor pressure is temperature dependent, the relative humidity is also very strongly dependent on temperature. The relative humidity increases with decreasing temperature and decreases with increasing temperature for a given absolute humidity. When the relative humidity is 100% the vapor saturation pressure and the dew point temperature have been reached. Therefore, with measurements of the relative humidity, the measuring sensor must be at the same temperature as the medium being measured. Temperature deviations of only one degree can result in serious measurement errors.

Special humidity chambers have been developed for carrying out such humidity dependent X-ray diffraction measurement of samples. The sample is introduced into the chamber and the chamber provided with appropriate windows for entrance and exit of X-rays. Flanges or feed elements are provided in the chamber for introduction of a humidified gas and heating devices are provided in close proximity to the sample to heat the sample to the desired temperature. In this manner, both the humidity of the environment of the sample within the specialized humidity chamber as well as the sample temperature can be controlled in a defined fashion (see for example Anton Paar® GmbH, THC Temperature Humidity Chamber, "Relative Humidity and Medium Temperature Attachment", Graz, Austria, May 2000, Company Brochure and Product).

In order to prepare the humidified gas for introduction into such chambers a so-called membrane humidifier tube or nested tubes have been used. Such double-tubed instruments are for example provided by the company PERMA PURE® (MH and PH®—Serres Humidifiers, PERMA PURE® Incorporated, Company Brochure, Novembre 1998) and are based on the use of a special material referred to in the industry as Nafion®. For such membrane humidifiers, water introduced to the outer side of the membrane comes into contact with and is spontaneously bound to sulphonic acid groups located within the membrane. In consequence thereof additional sulphonic acid groups located further within the membrane have a higher relative affinity to water than the groups already containing water and the water is consequently transported through ion channels until the opposite side of the membrane is reached and the membrane wall is saturated. This transport procedure occurs rapidly in the direction of the partial water pressure gradient. If liquid water is present on one side of the membrane and a flowing dry gas on the other side, a so-called "permeation distillation" can occur, since only water molecules can be transported through the ion channels. "Contaminants" in the water cannot therefore be transported into the gas. As long as the temperature of the gaseous portion of the instrument does not fall below the dew point temperature only water vapor can be present in the gas. The water transport properties depend on the temperature and on the flow of the gas that is to be moistened as well as on the length (the surface area) of the membrane tube. For advantageous configurations, the water pressure saturation point can be approached at high temperatures.

Such permeation distillation membrane humidifiers typically have a double tube construction in which the gas is present in an inner tube and water in the outer tube or vice versa. This double walled structure facilitates the application of moisturized gases to samples under positive pressures as well as to samples under vacuum. The water can be stationary or caused to flow in either the inner or outer tube and the flow rate of the gas can be adjusted in order to provide a humidity dependence as a function of various parameters. The inner tube is fashioned from the membrane humidifier and the outer tube typically from a corrosion resistance material.

Such moisturizing systems for use in X-ray diffraction spectrometer comprising a double tubed membrane humidifier system in combination with a specialized temperature humidity chamber have the disadvantage of being relatively sensitive to small changes in the operation parameters while only allowing certain restricted ranges of humidity at associated temperatures. In addition to the limitations concerning the temperatures and humidities at which samples can be measured, such systems tend to be expensive and complicated to construct and to use.

In view of these deficiencies in the prior art, it is the object of the present invention to present a method and apparatus for humidifying gases, in particular for use in X-ray diffraction spectrometers with which broad ranges of temperatures and humidity can be achieved using straight forward, stable, and relatively inexpensive technical means.

SUMMARY OF THE INVENTION

This object of the invention is achieved in an X-ray analysis system for controlling the humidity of the sample as well as in a method for its operation involving means for dividing a flowing gas stream into a first gas portion and a second gas portion, means for flowing this first gas portion through the membrane humidifier tube such that the first gas portion absorbs water passing through the inner wall of the tube, and with means for reuniting the first gas portion and the second gas portion into a moisturized gas stream and means for spraying said moisturized gas stream onto the sample as well as means for removing excess moisturized gas from the sample region to avoid condensation of gas humidity proximate the sample.

A particularly preferred X-ray system further comprises means for submerging a tube made from a membrane humidifier into a water bath, an outer wall of the tube being in direct contact with the water of said water bath, wherein water in the water bath is transported from the outer wall to an inner wall of the tube.

In contrast to prior art use of the double-walled tube, with the inner tube made from a membrane humidifier this preferred version of the instant invention proposes direct submersion of such a tube in a water bath. The transport of water through the walls of the membrane humidifier into the gas flowing through the inside of the humidifier can be controlled by controlling the temperature of the water bath in order to obtain humidified content of the gas which is close to saturation.

According to the invention, the humidified gas is not introduced into a sealed chamber to create a humidified environment completely surrounding the sample, rather is directly sprayed onto the sample, with excess moisturized gas being removed from the chamber. In this manner, the moisturized gas is presented to the sample in a continuous flow. The sample is therefore not disposed in a sealed chamber whose overall moisture content is controlled, rather is subjected to a continuous flow or "shower" of moisturized gas, the excess quantities of which are continuously removed from the chamber. This dynamic flow situation, in associated with the direct submersion of the membrane humidifier in a water bath provides for a moisturizing method and apparatus which is capable of achieving very high levels of moisture over a wide range of controlled temperatures thereby permitting wide ranging investigations of the materials of interest.

In a further preferred embodiment of the X-ray analysis system, the means for dividing the flowing gas stream into a first gas portion and a second gas portion comprise a first mass flow controller for the first gas portion and a second mass flow controller for the second portion. This measure has the advantage of being able to precisely control the amount of gas (in units such as ml/min) flowing through each of the two branches such that, subsequent mixture of the two gas streams following passage of the one gas stream through the water bath can lead to precise humidity content of the combined gas flow.

In a preferred variation of this latter embodiment, the first mass flow controller and the second mass flow controller are adjusted to maintain a constant combined moisturized gas flow. This measure has the advantage of maintaining a constant total gas flow onto the sample, independent of the humidity content of the moisturized gas to stabilize measurement conditions of the sample for improved quality and reproducibility of the resulting data.

In an additional preferred embodiment of the invention, the apparatus further comprises a first heater for changing the temperature of the water bath. This measure has the advantage of providing a capability of varying the rate of transport of the water through the walls of the membrane humidifier, since such transport is temperature dependent. This thereby allows control of the absolute humidity content of the gas flowing through the membrane humidifier to allow moisture contents approaching saturation values.

In an additional preferred embodiment of the invention, the reuniting means comprise a block into which the first gas portion and the second gas portion flow as well as means for maintaining an elevated temperature of that block. This measure has the advantage of providing a uniform recombination of the two mass flows at a stabilized temperature to avoid condensation of water vapor within the moisturized gas flow thereby preventing undesired effects of inadvertent dampening of the sample as a result of exposure to liquid water.

In a preferred embodiment of the invention, the membrane humidifier comprises Nafion®. This measure has the advantage of using a technologically high quality as well as commercially readily available material to effect the desired membrane humidification.

A further preferred embodiment of the invention provides that the introducing means comprise a second heater means for heating the moisturized gas stream along a path disposed between the reuniting means and the sample. This measure has the advantage of providing the capability of heating the humidified gas to a desired temperature for performance of measurements at the sample location with a desired humidity and temperature while avoiding problems associated with possible condensation of water vapor.

In a particularly preferred embodiment, the introducing means comprise nozzles in close proximity to the sample for spraying the moisturized gas stream onto the sample. In preferred embellishments of this embodiment, the nozzles are distributed about the sample in a symmetric fashion. Use of nozzles appropriately distributed in proximity to the sample allows for uniform flow of moisturized gas onto the sample for a homogeneous moisturization of the sample resulting in higher quality data, since all fractions of the sample exposed to the X-ray beam have substantially equal moisturization.

In a preferred embodiment of the invention, the excess moisturized gas removing means comprises an adjustable gas exhaust. This embodiment has the advantage of being able to control the rate at which moisturized gas is removed from the chamber to avoid complications associated with an excessive rate of moisturized gas removal which would result in inhomogeneous moisturization of the sample as well as with an inadequate moisturized gas removal which could result in condensation in regions of the apparatus in the immediate proximity of the sample.

An additional preferred embodiment the apparatus further comprises means for heating the sample to a constant temperature above the dew point temperature of the moisturized gas stream. This measure provides the capability of heating the sample to a temperature that safely avoids condensation of moisture on the sample or in its immediate vicinity.

In a further preferred embodiment, the apparatus further comprises means for measuring the humidity of the moisturized gas stream at the sample location. This measure has the advantage of providing constant monitoring of the humidity of the moisturized gas during the course of a given measurement. In embellishments of this embodiment, the means for measuring the moisturized gas stream can be coupled back to the mass flow controllers in order to provide a feedback regulation of the humidity.

In a preferred variation of this latter embodiment, the measuring means comprise a capacitive sensor having a water absorbing polymeric dielectric and an integrated temperature sensor. This measure has the advantage of providing a stable, sensitive, and accurate measurement of the relative humidity directly at the sample location that has good linearity properties and low susceptibility to malfunction.

In a further preferred embodiment of the invention, the emerging means comprises a chamber within which the water bath is disposed, the chamber having means for filling the water bath and means for venting the chamber. This measure has the advantage of straightforward capability for refilling the water bath in the event of excessive evaporation of the water. In embellishments thereof, control sensors can be placed within the chamber for monitoring the level of the water and for signaling filling thereof. The gas displaced during the filling process is vented through the venting means provided in the chamber.

In a further preferred embodiment of the invention, the X-ray analysis system further comprises a valve disposed between an output of the membrane humidifier tube leaving the water bath and the reuniting means and further comprises a condenser communicating with that valve to pass the moisturized, first gas portion through the condenser during a warm-up stage, a heating-up stage and a rinsing stage of the apparatus. This measure has the advantage of passing the moisturized first gas portion directly through a condenser and not into the sample chamber during initial phases in which the apparatus is being brought into operation and also facilitates rinsing the moisturized tube portion of the apparatus prior to introduction of the resulting moisturized gas to the sample.

In a preferred embodiment of the invention, the apparatus further comprises valve means disposed between the dividing means and the combining means to control flow of said second gas portion. This measure has the advantage of blocking passage of the gas to the uniting means during stages of operation of the apparatus in which the moisturized gas is not being introduced onto the sample.

In a further preferred embodiment of the invention, the X-ray analysis system further comprises means for controlling the dividing means in dependence on the moisture of said moisturized gas stream at the sample to regulate that moisture. This embodiment provides the advantage of feedback control of the moisture content through monitoring of the actual moisture content present at the sample to stabilize operation and provide improved homogeneity of the measurement results.

Further important aspects and details concerning the invention can be derived from the subsequent description of the drawing as well as from the features of the following claims. Such features and details can be important to the invention either individually or collectively in arbitrary mutual combination. Moreover, the embodiment shown below is not to be considered an exhaustive enumeration of all inventive features rather has exemplary character only for illustrating the invention.

BRIEF DESCRIPTION OF THE PREFERRED EMBODIMENT

Figure 1:
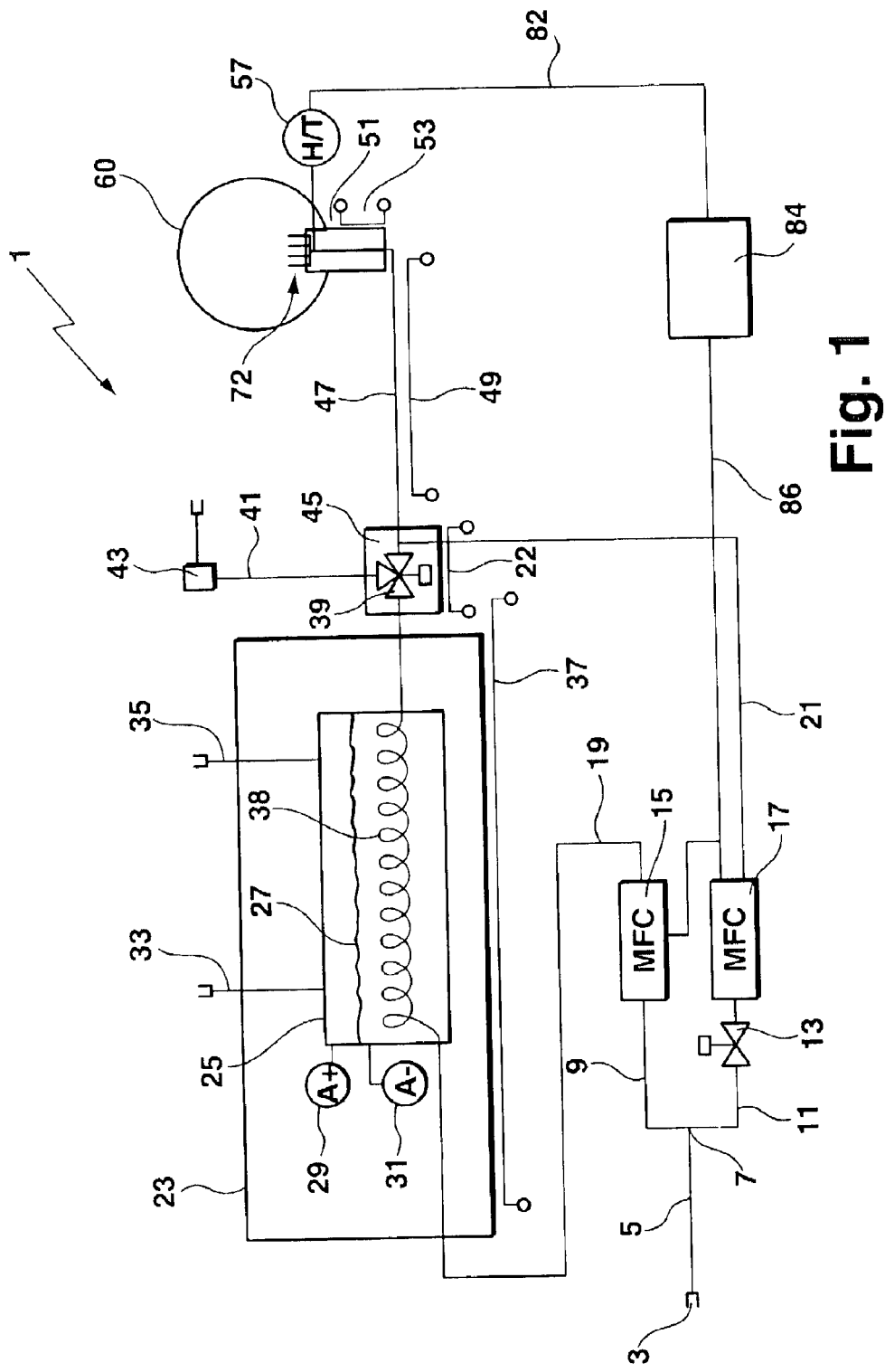
FIG. 1 shows an overall block diagram view of the apparatus in accordance with the invention.

FIG. 1 shows an overall view of the X-ray analysis system 1 in accordance with the invention. A gas source 3 is used to introduce pressurized gas into a first conduit 5. The pressurized gas can, for example, be at a pressure of 8 atm and means can be provided, for reducing this pressure to approximately 2 atm. The pressurized gas, of optionally reduced pressure, is passed through the first conduit 5 to a branch point 7 at which the gas is split into two gas flow portions. A second conduit 9 accepts a first gas flow portion and a third conduit 11 accepts the second gas flow portion. A valve can be disposed downstream of the third conduit 11 for shutting off the second gas flow portion if desired for reasons to be discussed in greater detail below. Immediately downstream of the second conduit 9 and the valve 13 are first mass flow controller 15 and second mass flow controller 17 respectively. The mass flow controllers 15, 17 can be used to adjust a precise degree of flow of the gas in the two branches thereby providing for a subsequent, precise remixture of the gas flows for controlling the humidity and moisture content of the resulting mixture. In particular, the mass flow controllers 15, 17 can be adjusted such that the total mass flow remains constant. For example, when the mass flow of mass flow controller 15 is increased, the mass flow controller 17 is decreased accordingly by an equal amount such that the overall gas flow remains constant. This improves the stability of the gas flow introduced onto the target and renders the moisturization process more homogeneous, resulting in higher quality data.

A fourth conduit 19 transports the first portion of gas passing through the mass flow controller 15 and a fifth conduit 21 accommodates the mass flow passing from the second mass flow controller 17. The first mass flow portion flowing through conduit 19 passes into a humidifier chamber 23. In particular, the humidifier chamber 23 contains a water bath 25 filled with water 27 to assume an appropriate water level. The water level is controlled by a maximum level sensor 29 and a minimum level sensor 31 which signal filling of the water 27 through a water fill inlet 33. As water is filled through the water fill 33, displaced gas can be vented through a vent 35. The water 27 present in the water bath 25 can be brought to a desired temperature by means of a second heater 37. The first gas portion passing through the fourth conduit 19 and entering into the water bath 25 connects with a membrane humidifier 38. The membrane humidifier 38 is in the form of a tube that, if desired, can be spirally wound within the water bath 25 to assume a desired length for moistening the first gas portion by an amount that approaches saturation.

A three way valve 39 is disposed downstream of the water bath 25 on a first block 45 heated by a first heater 22. The three way valve 39 can pass the first gas stream moisturized in the water bath 25 to a sixth conduit 41 leading to a condenser 43. In such a mode of operation, the humidified gas circuit can be cleaned or the system warmed up. The first block 45 is preferentially maintained at a controlled temperature of up to 100° C. The fifth conduit 21 transporting the second gas portion downstream of the second mass flow controller 17 joins into the first block 45 to recombine the two gas streams. Downstream of block 45, the combined gas flow, with its associated moisture content, is passed to a seventh conduit 47 for transport to the sample. A third heater 49 is positioned proximate the seventh conduit 47 to heat the moisturized gas flow to a desired temperature. The seventh conduit 47 feeds into a second block 51 located proximate the sample location which is maintained at a desired temperature by means of a fourth heater 53. The moisturized gas 51 is incident on a sample through nozzles 72 positioned in close proximity to the sample. A sensor means 57 monitors the humidity and temperature of the sample. This humidity and temperature information can be passed via a first communication path 82 from the sensor means 57 to a computing means 84. The computing means 84 can process this information and pass control signals via a second communication path 86 to appropriate devices on the first and second mass flow controllers 15, 17 to control the ratio of gas passing through the two controllers and thereby the overall moisture content of the resulting combination. In this manner, a feedback control of the mass flow controllers can be used to stabilize the resulting moisture of the gas which is sprayed onto the sample.

Figure 2:
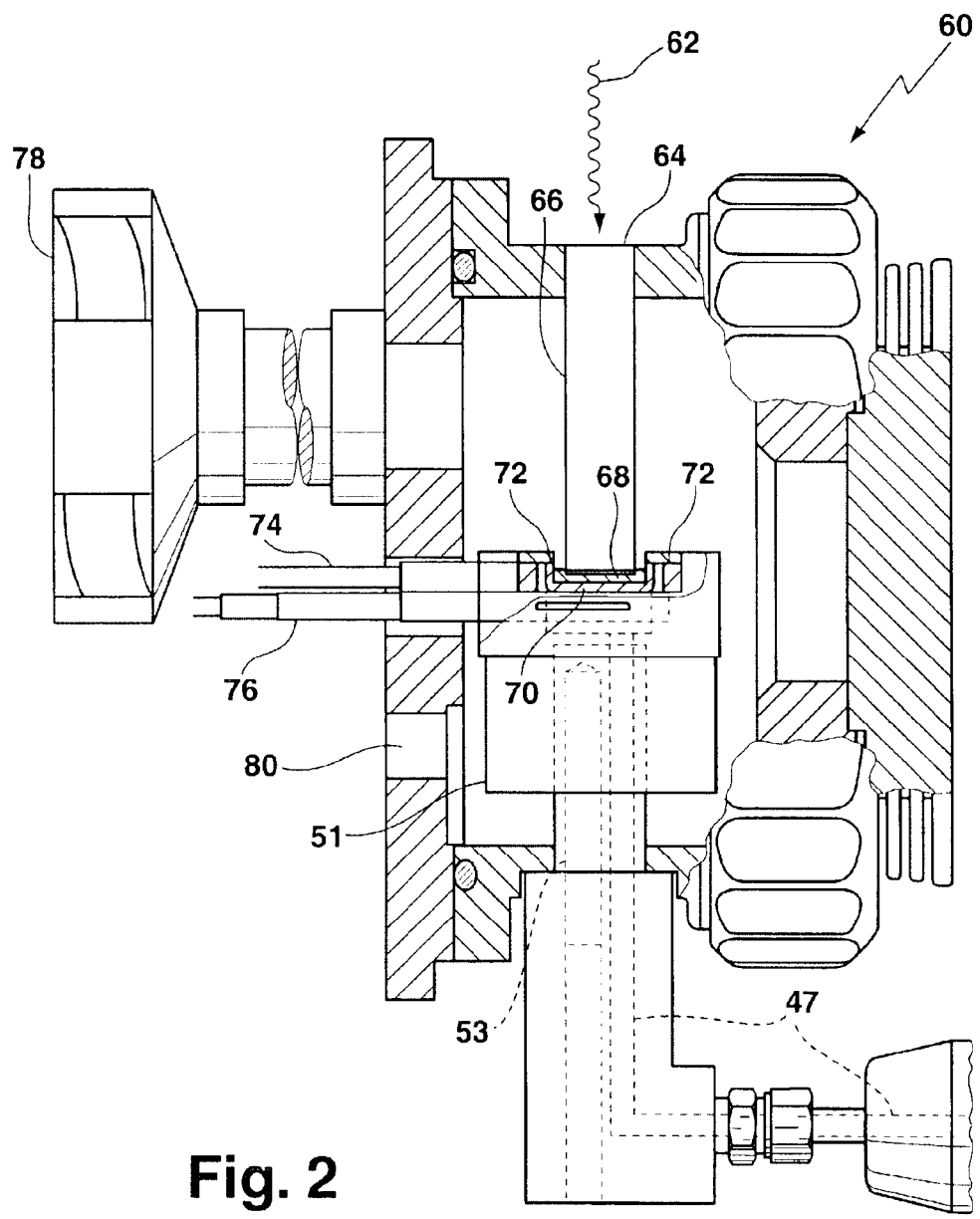
FIG. 2 shows an enlarged view of the chamber region at the sample location at which the humidified gas is applied to the sample.

FIG. 2 shows an exploded view of the sample region of the apparatus. A sample chamber 60 accepts incident X-ray radiation 62 which can both enter and leave the sample chamber 60 through appropriate windows, schematically indicated as 64. Means can be provided for passing the X-rays through an appropriate tube member 66 such that the X-rays can pass to the sample location within an environment differing from the ambient environment within other portions of the chamber. In particular, the ambient environment within the overall sample chamber 60 can contain moisturized gas such as nitrogen, whereas the X-rays passing through the X-ray passage tube 66 may be either in vacuum or i.e. helium. The window 64 can be made from appropriate material such as Kapton® or beryllium. The sample is positioned at an end of the X-ray passage tube 66 diametrically across from initial window 64. Nozzles 72 spray the moisturized gas onto the sample 68 in a controlled fashion. Symmetric configuration of the nozzles 72 can be used to homogenize the environment of the sample to provide for uniform moisturization thereof. A first sensor 74 used to control a sample temperature and a second sensor 76 measures both the relative humidity as well as the temperature at the sample location using capacitive means having a dielectric that is moisture absorbent. The chamber can be vented through a vent opening 80.

LIST OF REFERENCE SYMBOLS

| | |
|---|---|
| 1 | X-ray analysis system |
| 3 | gas source |
| 5 | first conduit |
| 7 | branch point |
| 9 | second conduit |
| 11 | third conduit |
| 13 | valve |
| 15 | first mass flow controller |
| 17 | second mass flow controller |
| 19 | fourth conduit |
| 21 | fifth conduit |
| 22 | first heater |
| 23 | humidifier chamber |
| 25 | water bath |
| 27 | water |
| 29 | maximum level sensor |
| 31 | minimum level sensor |
| 33 | water fill |
| 35 | vent |
| 37 | second heater |
| 38 | membrane humidifier |
| 39 | three way valve |
| 41 | sixth conduit |
| 43 | condenser |
| 45 | first block |
| 47 | seventh conduit |
| 49 | third heater |
| 51 | second block |
| 53 | fourth heater |
| 57 | sensor means |
| 60 | sample chamber |
| 62 | X-rays |
| 64 | window |
| 66 | X-ray passage tube |
| 68 | sample |
| 70 | sample holder |
| 72 | nozzles |
| 74 | first sensor |
| 76 | second sensor |
| 78 | adjustable gas exhaust |
| 80 | chamber vent |
| 82 | first communication path |
| 84 | computing means |
| 86 | second communicating path |

We claim:

1. An X-ray analysis system for controlling the humidity of a sample, the system comprising:
   means for dividing a flowing gas stream into a first gas portion and a second gas portion;
   means for flowing said first gas portion through a membrane humidifier tube such that said first gas portion absorbs water vapor passing through an inner wall of said tube;
   means for combining said first gas portion and said second gas portion into a moisturized gas stream;
   means for spraying said moisturized gas stream onto said sample; and
   means for removing excessive moisturized gas from a vicinity of said sample to avoid condensation of gas humidity proximate said sample.

2. The X-ray analysis system of claim 1, the system further comprising means for submerging said membrane humidifier tube into a water bath, an outer wall of said tube being in direct contact with water of said water bath, wherein water in said water bath is transported from said outer wall to said inner wall of said tube.

3. The X-ray analysis system of claim 1, wherein said dividing means comprise a first mass flow controller for said first gas portion and a second mass flow controller for said second gas portion.

4. The X-ray analysis system of claim 3, wherein said first mass flow controller and said second mass flow controller are adjusted to maintain said combined moisturized gas stream at constant flow.

5. The X-ray analysis system of claim 2, further comprising first heater means for changing a temperature of said water bath.

6. The X-ray analysis system of claim 1, wherein said combining means comprise a block into which said first gas portion and said second gas portion flow as well as means for maintaining an elevated temperature of said block.

7. The X-ray analysis system of claim 2, wherein said membrane humidifier of said tube comprises $$-\{(CF_2)_m-\underset{|}{CF}-CF_2\}_n$$
$$\{O-CF_2-\underset{|}{CF}-CF_3\}_2$$
$$O-CF_2-CF_2-SO_3H\cdot\{H2O\}_x.$$

8. The X-ray analysis system of claim 1, wherein said spraying means comprises a second heater means for heating said moisturized gas stream along a path disposed between said combining means end the sample.

9. The X-ray analysis system of claim 1, wherein said spraying means comprise nozzles in close proximity to the sample for spraying said moisturized gas stream onto said sample.

10. The X-ray analysis system of claim 1, wherein said excessive moisturized gas removing means comprise an adjustable gas exhaust.

11. The X-ray analysis system of claim 1, further comprising means for heating the sample to a constant temperature above a dew point temperature of said moisturized gas stream.

12. The X-ray analysis system of claim 1, further comprising means for measuring a humidity of said moisturized gas stream at the sample.

13. The X-ray analysis system of claim 12, wherein said humidity measuring means comprise a capacitive sensor having a water absorbing polymeric dielectric and an integrated temperature sensor.

14. The X-ray analysis system of claim 2, wherein said submerging means comprise a chamber within which said water bath is disposed, said chamber having means for filling said water bath and means for venting said chamber.

15. The X-ray analysis system of claim 2, further comprising a valve disposed between an output of said membrane humidifier tube following said water bath and said combining means and with a condenser communicating with said valve to pass said first gas portion through said condenser during at least one of warm up, heating up, and rinsing.

16. The X-ray analysis system of claim 1, further comprising valve means disposed between said dividing means and said combining means to control flow of said second gas portion.

17. The X-ray analysis system of claim 1, further comprising means for controlling said dividing means in dependence on a moisture of said moisturized gas stream at the sample to regulate said moisture.

18. A method for operating an X-ray analysis system to control the humidity of a sample, the method comprising the steps of:
   a) dividing a flowing gas stream into a first portion and a second portion;
   b) flowing said first gas stream portion through a membrane humidifier tube such that said first gas portion absorbs water vapor passing through an inner wall of said tube;
   c) reuniting said first portion and said second portion into a moisturized gas stream following step b);
   d) spraying said moisturized gas stream onto said sample; and
   e) removing excessive moisturized gas from a region of said sample to avoid condensation of gas humidity proximate said sample.

19. The method of claim 18, the method further comprising the step of:
   a1) submerging said membrane humidifier tube into a water bath, an outer wall of said tube being in direct contact with water of said water bath, wherein water in said water bath is transported from said outer wall to said inner wall of said tube.

* * * * *